United States Patent [19]

Watts

[11] 4,274,437

[45] Jun. 23, 1981

[54] HEART VALVE

[76] Inventor: Len S. Watts, 510 Hastings Dr., Benicia, Calif. 94510

[21] Appl. No.: 125,481

[22] Filed: Feb. 28, 1980

[51] Int. Cl.³ .......................... F16K 15/03; A61F 1/22
[52] U.S. Cl. ...................................... 137/527; 3/1.5; 137/512; 251/212
[58] Field of Search ............. 3/1.5, 1; 137/527, 527.8, 137/512; 251/212

[56] References Cited

U.S. PATENT DOCUMENTS

| | | | |
|---|---|---|---|
| 3,370,305 | 2/1968 | Goott et al. | 3/1.5 |
| 4,078,268 | 3/1978 | Possis | 3/1.5 |
| 4,159,543 | 7/1979 | Carpentier | 3/1.5 |
| 4,178,638 | 12/1979 | Meyer | 3/1.5 |
| 4,178,639 | 12/1979 | Bokros | 3/1.5 |

FOREIGN PATENT DOCUMENTS 2846299  5/1979  Fed. Rep. of Germany ............... 3/1.5

*Primary Examiner*—Ronald L. Frinks
*Attorney, Agent, or Firm*—Fitch, Even, Tabin, Flannery & Welsh

[57] ABSTRACT

A heart valve prosthesis has an annular valve body and two curved leaflets which are pivotally mounted for movement between open and closed positions. A 360° groove is provided in the interior surface of the valve body, and spherical pivots projecting from opposite sides of the leaflets are pivotally received in the groove. The valve functions as a check valve, and the flow reversal which occurs during the pumping strokes of the heart causes the leaflets to pivot from one position to the other. As the leaflets pivot, they orbit about the axis of the valve eliminating localized wear which could otherwise occur at the locations in the valve body against which the rotating pivots would bear.

10 Claims, 7 Drawing Figures

U.S. Patent
Jun. 23, 1981
4,274,437
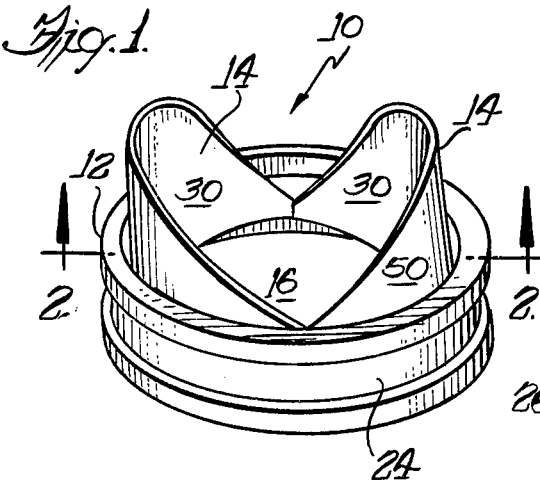
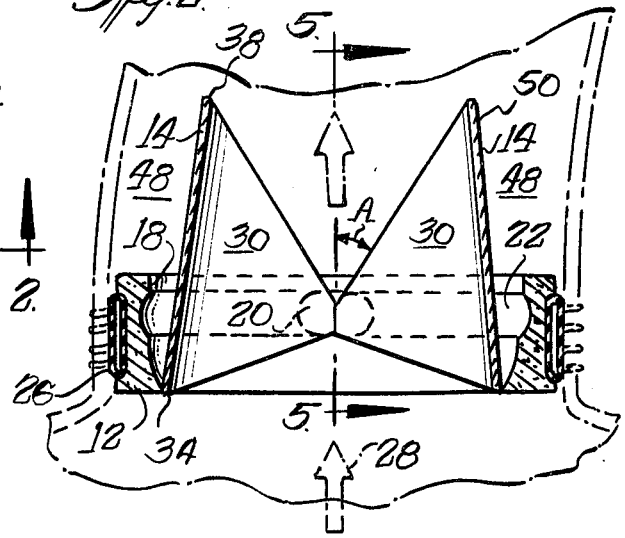
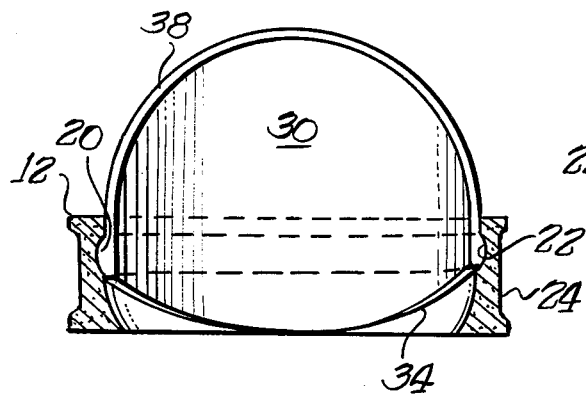
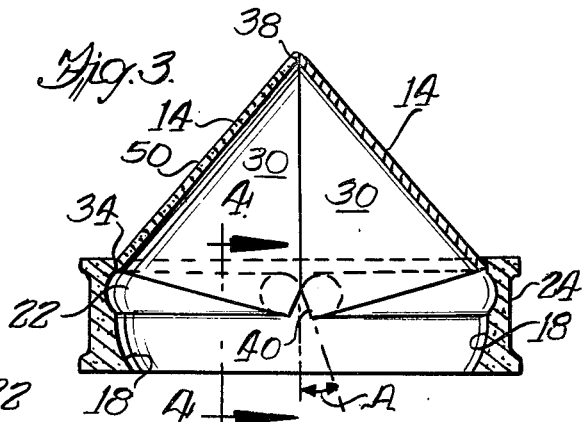
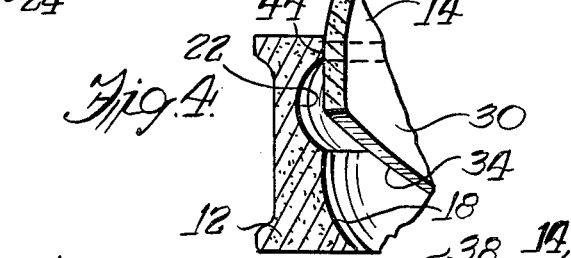
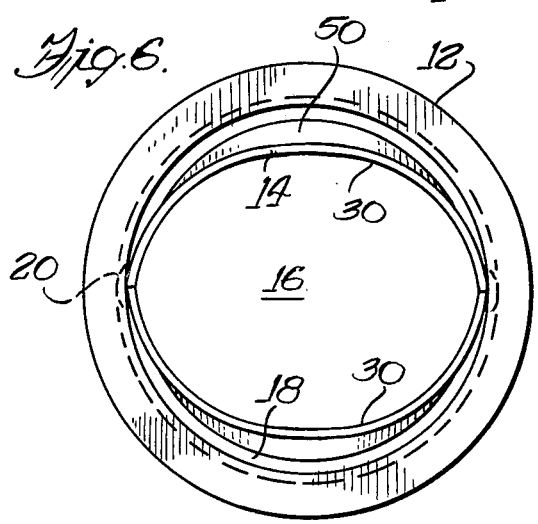
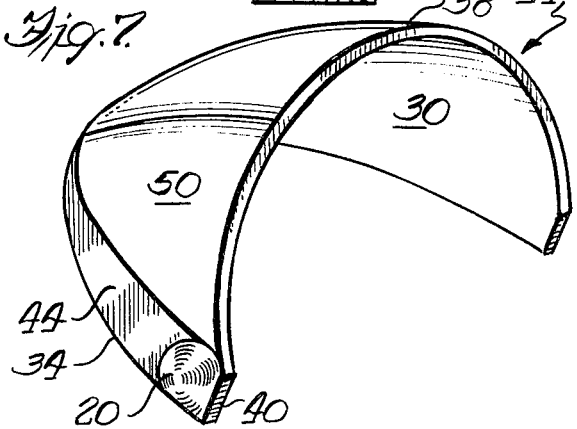

HEART VALVE

BACKGROUND OF THE INVENTION

The invention relates to check valves and more particularly to check valves designed to function as a heart valve prosthesis.

A wide variety of heart valves have been developed that operate hemodynamically as a result of the pumping action of the heart. Some of the earliest valves were of the ball and cage design, as exemplified by U.S. Pat. No. 3,416,159, issued Dec. 17, 1968. Thereafter, a wide variety of valves which utilized one or more disc-shaped occluders were developed, as exemplified by U.S. Pat. No. 3,367,364, issued Feb. 6, 1968. Somewhat more recently, valves utilizing a pair of pivoting leaflets were developed—such as those shown in U.S. Pat. No. 4,159,543, issued July 3, 1979, and in U.S. Pat. No. 4,178,639, issued Dec. 18, 1979. U.S. Pat. No. 4,178,638, issued Dec. 18, 1979, is exemplary of a heart valve using a pair of curved leaflets which pivot about central hinge points.

The fairly large number of patents in this area is evidence of the fact that the search goes on for improved heart valves which have prompt response, exhibit low pressure drop in the open position and do not develop localized wear.

BRIEF SUMMARY OF THE INVENTION

A heart valve has been developed that utilizes a pair of curved leaflets which pivot to locations in the open position providing a wide-open, central flow path through the annular valve body. The valve is responsive to the end of a pumping stroke of the heart and quickly moves to the closed position where there is extremely little leakage. Localized wear is minimized because, while the leaflets pivot between the open and closed positions, they jointly slowly orbit in a circle about the axis of the valve passageway.

BRIEF DESCRIPTION OF THE DRAWINGS

FIG. 1 is a perspective view of a heart valve embodying various features of the invention wherein the leaflets are shown in the open position;

FIG. 2 is a sectional view taken generally along a line 2—2 of FIG. 1 showing the heart valve mounted in the aortic position;

FIG. 3 is a sectional view similar to FIG. 2 of the heart valve alone shown with the leaflets in the closed position;

FIG. 4 is a fragmentary sectional view taken generally along the line 4—4 of FIG. 3;

FIG. 5 is a sectional view taken generally along the line 5—5 of FIG. 2;

FIG. 6 is a plan view of the valve shown in FIG. 1 with the leaflets in the open position; and FIG. 7 is a perspective view, enlarged in size, of one of the leaflets from the valve shown in FIG. 1.

DETAILED DESCRIPTION OF THE PREFERRED EMBODIMENT

Illustrated in the drawings is a heart valve 10 which has an annular valve body 12 that carries a pair of leaflets or valve members 14 which hemodynamically pivot between opened and closed positions to control the flow of blood through the central passageway 16 defined by the interior surface 18 of the annular valve body 12. Each of the leaflets 14 carries a pair of pivots 20 which are preferably sectors of a sphere that are received in a groove 22 formed in the interior surface 18 of the annular valve body.

The annular valve body 12 can be formed from any suitable biocompatible material and is preferably provided with a peripheral recess 24 in its outer surface which accommodates a suturing ring 26 that facilitates its suturing to the heart tissue. The cross section of the passageway 16 through the annular valve body, defined by the interior surface 18, is preferably circular. The axis or center line of the valve body 12 illustrated in the drawings is vertical; however, it should be understood that the valve 10 can operate in any orientation because it is not significantly affected by gravity. In the illustrated embodiment, the normal flow of blood on the pumping stroke of the heat is in the upward direction, as depicted by the arrows 28, in FIG. 2 which shows the leaflets 14 in the open position with normal blood flow occurring therethrough.

The leaflets 14 may also be made of any suitable material that is biocompatible and nonthrombogenic and which will withstand wear under countless cycles of opening and closing to which a heart valve will of course be subjected. Isotropic graphite, such as that sold under the tradename POCO, which has been suitably coated with dense pyrolytic carbon, such as that sold under the tradename PYROLITE, is preferred for the leaflets and for the valve body. The leaflets 14 are curved in cross section and have a concave surface 30 which is a surface of revolution and which faces inward in the assembled valve. Preferably, the leaflets 14 are sections of a hollow right circular cylinder or tube, and the convex outer surfaces are surfaces of revolution.

The pivots 20 mount the leaflets 14 eccentrically and extend outward from the lateral sides of each leaflet in opposite directions along a common axis, transverse to the centerline of the passageway 16. The pivots 20 are sectors of a body of revolution which is preferably a sphere but which could be an ellipsoid, a hyperboloid or a paraboloid. The surface of the groove 22 is complementary to the contour of the pivots 20, and preferably the radius of curvature of the groove is just slightly larger than the radius of curvature of the pivots so that the pivots can rotate freely within the groove and can also orbit as explained hereinafter.

The outer edge of the upstream end 34 of the convex outer surface of the leaflets is substantially semi-circular and is designed to seal against the interior surface 18 of the annular valve body, against which it wipes. Accordingly, the interior surface 18 of the annular valve body 12, exclusive of the groove 22, is a section of a generally spherical surface, the center of which lies on the center line of the valve in the horizontal plane through the center of the groove 22. As a result of this construction, the outer edge of the upstream end of the leaflets 14 seals against the valve body interior surface 18, both in the open position, as illustrated in FIG. 2, and in the closed position, as illustrated in FIG. 3 and as discussed in more detail hereinafter.

The downstream ends of both of the leaflets 14 terminate in matching surfaces 38 which abut along the entire length thereof between the pivots 20 in the closed position and provide the desired seal between the leaflets across the valve passageway 16. The surfaces 38 are preferably planar (as best seen in FIG. 2); however, they could be rounded and abut in line contact. Both leaflets 14 preferably have the same shape; however, the downstream end of one could have protrusions which are received in matching indentations of the other leaflets so long as the end surfaces 38 abut.

In pivoting between the open and the closed positions, each of the leaflets 14 pivots an amount equal to the angle A, which is preferably between about 30° and 45°. Angle A in FIG. 2 is of course equal to the angle A in FIG. 3 which is the angle between a plane through the center line of the valve and a pair of flat surfaces 40 formed on each leaflet 14 in the region of the pivots. The flat surfaces 40 determine the amount of pivotal movement which occurs when the leaflets 14 swing to the open position because these surfaces 40 serve as stops which abut each other and thus halt movement of the desired orientation in the open position.

To assure that a good seal is provided between the periphery of each of the leaflets 14 and the interior valve surface 18 when the leaflets are in the closed position depicted in FIG. 3, thickened regions 44, as best seen in FIG. 7, are provided along the upstream ends of the leaflets 14. As can be seen in FIG. 3, when the leaflets are in the closed position, the center portions of the semicircular upstream edges 34 seal against the interior surface 18 of the valve body in the relatively narrow region downstream of the groove 22 (above the groove in FIG. 3). However, the remainder of the semicircular edges 34 lie in the vicinity of the groove and thus would allow the back flow of blood through the groove around the edge 34. As best seen in FIG. 4, the proportioning of the thickened sections 44 is such that they wipe against the narrow regions of the interior valve body surface 18 above the groove 22 and thus provide a very effective seal, past which there is extremely little back flow of blood.

In operation, when the heart begins the pumping stroke to force blood through a valve 10 mounted in the aortic position, the leaflets will initially be in the closed position depicted in FIG. 3. As soon as any significant blood pressure is applied to the concave surfaces 30 of the leaflets 14, its application to this relatively large surface area creates a prompt outward swinging or pivoting of the leaflets allowing blood flow to begin in the direction of the arrows 28. The leaflets 14 pivot outwards about their eccentric axes until the flat stops 40 abut each other. Because the curved surfaces 30 of the leaflets 14 are nearly parallel to the direction of flow of blood when they reach the outward or open position, there is very little force upon the abutting surfaces 40 and wear at this point is no problem.

When the pumping stroke of the respective ventricle ceases and contraction begins, blood pressure builds up on the downstream side of the valve, in the regions above the valve depicted in FIG. 2, which has the tendency to create back flow through the valve. Because there is a seal between the edge 34 of the leaflets and the interior surface 18 of the valve body, blood pressure quickly builds up in the region 48 (FIG. 2) between the wall of the aorta and the outer convex surface 50 of the leaflets. This pressure on the convex surface 50 of the leaflets is not counterbalanced by pressure on the concave inward surfaces 30 because the passageway through the valve is open and thus results in a force being applied against the convex surfaces of the leaflets. Because of the eccentric placement of the pivot axes, this force causes the leaflets 14 to pivot quickly to the closed position shown in FIG. 3.

Preferably, the design of the leaflets 14 is such that the center of gravity of each of the leaflets lies above a horizontal plane through the pivot points 40 when the leaflets are arranged in the open position. Because the center of gravity of each leaflet 14 lies above (i.e., on the downstream side of) the plane through the pivot points perpendicular to the axis of the annular valve body, the leaflets move quickly to the closed position as soon as any significant build-up of back flow pressure occurs in the regions 48 and therefore regurgitation through the valve 10 is minimized. As earlier indicated, in the closed position, the planar surfaces 38 at the downstream ends of the leaflets abut each other to provide the seal along the center of the passageway 16, whereas the seal at the periphery of the passageway is accomplished between the interior surface of the valve body 18 and the outer surface edge of each of the upstream ends of the leaflets 14 as described hereinbefore.

Because the planar surfaces 38 along the donwstream ends of the leaflets extend for a substantial distance, as best seen in FIG. 5, there is no localized wear when these surfaces abut in the closed position. The force of the back pressure of blood upon the leaflets 14 in the closed position is of course carried by the pivots 20 which bear against the interior surface of the groove 22 wherein they orbit. However, the design of the valve is such that the leaflets constantly change position within this 360° groove by orbiting in a circle about the center line through the valve. As the leaflets 14 are pivoting between the opened and closed positions, they are of course subject to the varying forces of the blood stream flowing past the interior concave surfaces 30, and the force of the flowing stream on the interior surfaces results in orbital movement of the pivots 20 in the circle defined by the groove 22. As a result of this constant change of position, localized wear within the groove is prevented, thus providing the valve with excellent life expectancy in addition to prompt responsiveness and extremely low leakage. These factors coupled with the extremely low pressure drop through the valve with the leaflets in the open position, as is strikingly illustrated by FIG. 6, provides a significantly improved heart valve prosthesis which has clearly visible advantages over heart valves currently being used.

Although the invention has been described with regard to a certain preferred embodiment which constitutes the best mode presently known to the applicant, it should be understood that various changes and modifications as would be obvious to one having the ordinary skill in this art may be made without departing from the scope of the invention which is defined solely by the claims appended hereto. For example, although the valve is designed to function as a heart valve, the design could be employed in other check valve applications. Particular features of the invention are emphasized in the claims which follow.

What is claimed is

1. A valve comprising
   an annular valve body having an interior surface which defines a central passageway therethrough for the flow of liquid in a predetermined direction generally along the axis of said passageway,
   said annular body having a groove in its interior passageway-defining surface which extends 360° therearound, and
   a pair of valve members proportioned to fit together and block flow through said passageway when in the closed position, said valve members each including two oppositely extending rounded pivots proportioned to be pivotally received in said groove, said valve members each having an outward facing convex surface, the upstream end of each of said valve members having a substantially semi-circular outward edge that seals against said interior surface of said valve body, whereby said valve members pivot between their open and closed positions as a result of fluid pressures developed at opposite ends thereof and as a result of said pivotal movement gradually orbit with respect to the axis of said valve body passageway.

2. A valve is accordance with claim 1 wherein said valve members are substantially sections of a cylindrical tube of right circular cross section.

3. A valve in accordance with claim 1 wherein said groove has a cross section of segment of a circle.

4. A valve in accordance with claim 3 wherein said pivots are sectors of a sphere.

5. A valve in accordance with claim 4 wherein said valve members in the regions adjacent said pivots have facing flat surfaces that abut each other and serve as stops for said valve members in the open position.

6. A valve in accordance with claim 1 wherein said valve members have inward facing planar surfaces at the downstream ends thereof which abut each other in the closed position.

7. A valve in accordance with claim 1 wherein said pivots define a pivotal axis for each leaflet that is eccentric thereof.

8. A valve in accordance with claim 1 wherein said seal between said semi-circular edges and said valve body interior surface is maintained in both the open and the closed positions.

9. A valve in accordance with claim 8 wherein each of said leaflets is formed with a region of greater thickness near its upstream end which in the closed position contacts said interior surface of said annular body at a location downstream of said groove to achieve said seal.

10. A valve in accordance with claim 8 wherein said leaflets are proportioned so that, in the open position, a plane perpendicular to the axis of said annular body and extending through said pivots lies downstream of the center of gravity of said leaflets.

* * * * *